United States Patent [19]
DeBernardis et al.

[11] Patent Number: 5,185,364
[45] Date of Patent: Feb. 9, 1993

[54] AMINOMETHYL-CHROMAN AND -THIOCHROMAN COMPOUNDS

[75] Inventors: John F. DeBernardis, Lake Villa; David L. Arendsen, Libertyville; Robert E. Zelle, Grayslake, all of Ill.

[73] Assignee: Abbott Laboratories, Abbott Park, Ill.

[21] Appl. No.: 786,150

[22] Filed: Oct. 31, 1991

Related U.S. Application Data

[60] Division of Ser. No. 543,782, Jan. 13, 1989, Pat. No. 5,089,519, which is a continuation-in-part of Ser. No. 144,363, Jan. 15, 1988, abandoned.

[30] Foreign Application Priority Data

Jan. 13, 1989 [WO] World Int. Prop. O. ............. PCT/US89/00141

[51] Int. Cl.$^5$ .................... A61K 31/38; C07D 409/06
[52] U.S. Cl. .................... 514/444; 549/60; 549/406; 548/525; 548/526; 514/456; 514/458; 514/422
[58] Field of Search ............... 549/60, 406; 514/444, 514/456, 458, 422; 548/525, 526

[56] References Cited

U.S. PATENT DOCUMENTS

| 4,066,648 | 1/1988 | Oka et al. ............. 544/151 |
| 4,563,458 | 1/1986 | Widdig et al. ............ 544/230 |
| 4,647,579 | 3/1987 | Kabbe et al. ............ 514/456 |
| 4,659,737 | 4/1987 | Kabbe et al. ............ 548/407 |

FOREIGN PATENT DOCUMENTS

| 114374 | 12/1983 | European Pat. Off. |
| 157267 | 3/1984 | European Pat. Off. |
| 59-110690 | 6/1984 | Japan |

OTHER PUBLICATIONS

A. Gilman, "The Pharmacological Basis of Therapeutics", 6th ed. pp. 186–187, MacMillan Publishing Co., Inc., New York (1980).

*Primary Examiner*—Richard L. Raymond
*Assistant Examiner*—Mark W. Russell
*Attorney, Agent, or Firm*—John F. DeBernardis; David L. Arendsen; Robert E. Zelle

[57] ABSTRACT

The present invention includes compounds represented by the formula:

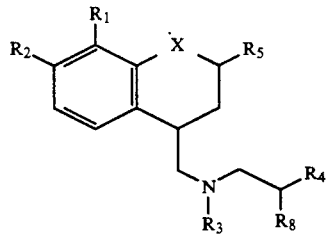

wherein
X is O or S;
$R_1$ and $R_2$ are independently selected from the group consisting of hydrogen, hydroxy, halo, loweralkoxy, thioalkoxy and loweralkyl; or $R_1$ and $R_2$ taken together can form a methylenedioxy or ethylenedioxy bridge;
$R_3$ is loweralkyl;
$R_4$ is selected from

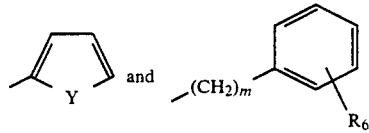

wherein Y is O or S, $R_6$ is hydrogen, methoxy or halo and m is 0 or 1;
$R_5$ is hydrogen, loweralkyl, phenyl or substituted phenyl wherein the phenyl ring is substituted with one, two or three substituents independently selected from loweralkyl, halo, hydroxy, loweralkoxy, amino and thioalkoxy; and
$R_8$ is hydrogen or $R_3$ and $R_8$ taken together form a pyrrolidine ring; or a pharmaceutically acceptable salt thereof.

6 Claims, No Drawings

AMINOMETHYL-CHROMAN AND -THIOCHROMAN COMPOUNDS

This application is a division of co-pending application Ser. No. 543,782 filed Jan. 13, 1989 as PCT/US89/00141, now U.S. Pat. No. 5,089,519, which is a continuation-in-part of U.S. patent application Ser. No. 144,363 filed Jan. 15, 1988, now abandoned.

Technical Field

This invention relates to alpha-2-adrenergic antagonists useful in the treatment of depression, metabolic disorders (e.g. obesity or diabetes), glaucoma, migraine and hypertension.

BACKGROUND OF THE INVENTION

The adrenergic nervous system plays a major role in the innervation of heart, blood vessel and smooth muscle tissue. Compounds capable of interacting with receptor sites within the adrenergic nervous system can initiate a variety of physiological responses, including vasoconstriction, vasodilation, and increased or decreased heart rate (chronotropic), contractility (inotropic) and metabolic activity. In the past, various adrenergic compounds have been employed to affect these and other physiological responses. However, many adrenergic compounds do not possess significant selectivity to enable desirable interactions with adrenergic receptor sites. That is, these adrenergic compounds do not demonstrate a high degree of specificity for differing receptor types within the adrenergic nervous system in order to obtain a desired physiological response separate from other possible, and perhaps less desirable, responses of the system.

Disclosure of the Invention

It has now been determined that a new class of compounds, as herein defined, demonstrate an ability to selectively inhibit (antagonists) alpha-2-adrenergic receptors which are mainly distributed on the membranes of central and peripheral adrenergic neurons and on the tissues innervated thereby.

Through inhibitory interaction with the alpha-adrenergic receptor in the peripheral nervous system, one can modulate the function of adrenergic neurons and hemodynamic equilibrium which is therapeutically useful in a multitude of cardiovascular indications such as hypertension, congestive heart failure, and a variety of vascular spastic conditions. Furthermore, the alpha-adrenergic antagonists are useful in certain neurological and psychiatric disorders such as depression.

The present invention includes compounds represented by the formula:

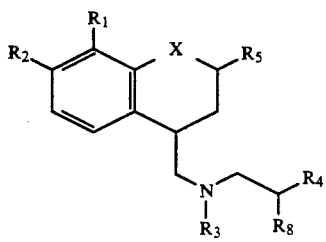

(I)

wherein X is O or S;
$R_1$ and $R_2$ are independently selected from the group consisting of hydrogen, hydroxy, halo, loweralkoxy, thioalkoxy and loweralkyl; or $R_1$ and $R_2$ taken together can form a methylenedioxy or ethylenedioxy bridge;
$R_3$ is loweralkyl;
$R_4$ is selected from

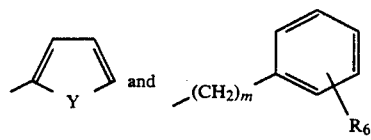

wherein Y is O or S, $R_6$ is hydrogen, methoxy or halo and m is 0 or 1;
$R_5$ is hydrogen, loweralkyl, phenyl or substituted phenyl wherein the phenyl ring is substituted with one, two or three substituents independently selected from loweralkyl, halo, hydroxy, loweralkoxy, amino and thioalkoxy; and
$R_8$ is hydrogen or $R_3$ and $R_8$ taken together form a pyrrolidine ring; or a pharmaceutically acceptable salt thereof.

It will be appreciated that the compounds of the present invention contain asymmetric carbon atoms and it is to be understood that the invention includes both the racemic mixture as well as the optically active derivatives.

As used herein, the term "loweralkoxy" refers to alkoxy groups containing 1 or 2 carbon atoms.

As used herein, the term "thioalkoxy" refers to —SR" wherein R" is an alkyl residue containing 1 or 2 carbon atoms.

As used herein, the term "loweralkyl" means straight or branched chain saturated hydrocarbon radicals having 1 to 3 carbon atoms, such as methyl, ethyl, n-propyl and iso-propyl.

As used herein, the term "substituted phenyl" means a phenyl ring with one, two or three substituents independently selected from loweralkyl, halo, hydroxy, loweralkoxy, amino and —$SR_7$ wherein $R_7$ is loweralkyl.

As used herein, the term "halo" or "halogen" means fluorine, iodine, bromine or chlorine.

The term "pharmaceutically acceptable salts" refers to the pharmaceutically acceptable, relatively nontoxic, inorganic or organic acid addition salts of the compounds of this invention. These salts can be prepared in situ during the final isolation and purification of the compounds, or by separately reacting the free base with a suitable organic or inorganic acid. Representative salts include the hydrochloride, hydrobromide, sulfate, phosphate, nitrate, bisulfate, acetate, oxalate, valerte, oleate, palmitrate, methanesulfonate, stearate, laurate, borate, benzoate, lactate, phosphate, tosylate, citrate, maleate, fumarate, succinate, tartrate, napsylate and the like It will be apparent to those skilled in the art that, depending upon the number of available amino groups for salt formation, the salt of this invention can be per N-salts.

The compounds of the present invention can be prepared as illustrated in Scheme 1.

As seen in Scheme 1, starting with the desired 4-chromanone derivative, treatment with trimethylsilyl cyanide, followed by dehydration with p-TsOH, affords the desired chromene derivative 2. Reduction to the aminomethyl derivative is accomplished with Raney Nickel (RaNi) or sodium borohydride followed by diborane, to give 3. $R_3$ can be introduced using the appropriate carboxylic acid or ester, activated ester or acid halide derivatives thereof, followed by reduction of the resulting amide bond. Acid halide derivatives include the acid chloride. Esters include the methyl and ethyl esters. Activated ester derivatives include activated esters commonly used by those skilled in the art for activating carboxylic acid groups for coupling with an amine to form an amide bond including, but not limited to, formic and acetic acid derived anhydrides, anhydrides derived from alkoxycarbonyl halides such as isobutyloxycarbonylchloride and the like, N-hydroxysuccinimide derived esters, N-hydroxyphthalimide derived esters, N-hydroxybenzotriazole derived esters, 4-nitrophenol derived esters, 2,4,5-trichlorophenol derived esters and the like. In particular, N-alkylation of 3 is accomplished with ethylformate or acetic anhydride, followed by diborane reduction, to give 4. The $R_4$ containing alkyl group can be introduced using the appropriate carboxylic acid or ester, activated ester or acid halide derivatives thereof as defined herein, followed by reduction of the resulting amide bond. In particular, dicyclohexylcarbodiimide promoted coupling of 4 with the appropriately substituted carboxylic acid, followed by reduction with lithium aluminum hydride or borane-tetrahydrofuran complex, affords the desired compound 5.

The compounds of the invention which contain a pyrrolidine ring can be prepared as illustrated in Scheme II.

As seen in Scheme II, starting with the previously described chromene derivative 2, reduction with sodium borohydride followed by hydrolysis of the resulting unsaturated nitrile with potassium hydroxide in refluxing ethylene glycol affords the desired carboxylic acid 6. The pyrrolidine substituent can be introduced via reaction with the carboxylic acid or an acid halide, ester or activated ester derivative as defined herein. In particular, dicyclohexylcarbodiimide promoted coupling followed by reduction of the resulting amide with lithium aluminum hydride or borane-tetrahydrofuran complex affords the desired compound 7.

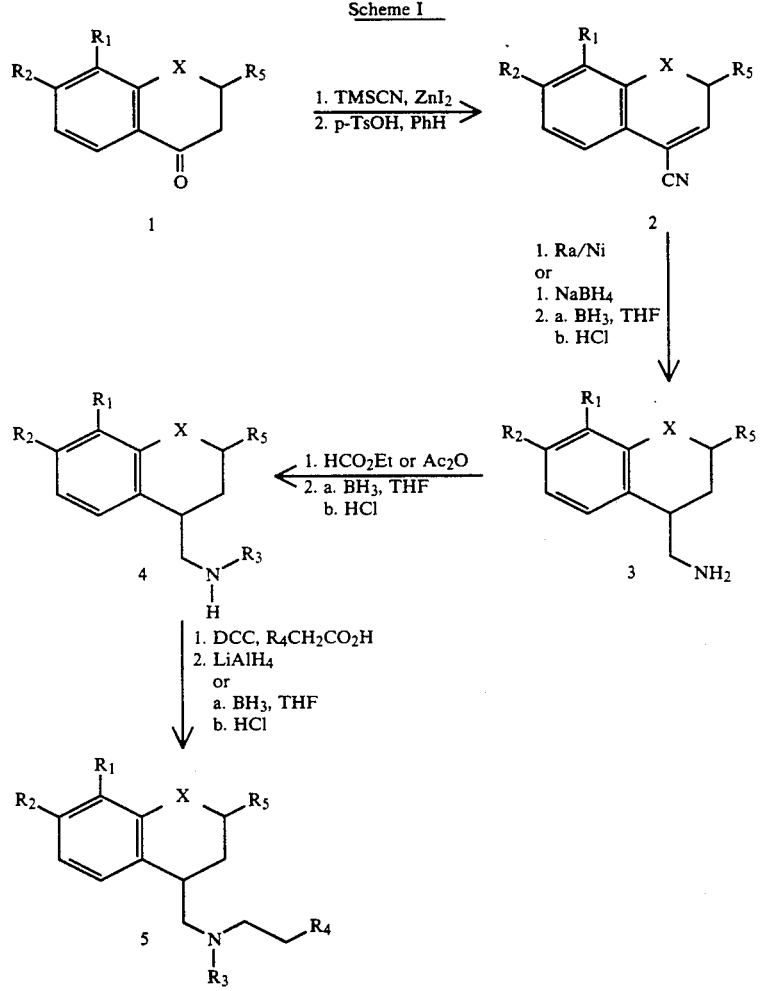

Scheme I

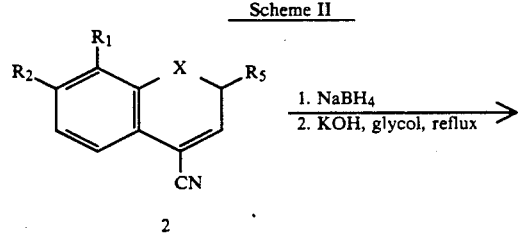

Scheme II

-continued
Scheme II

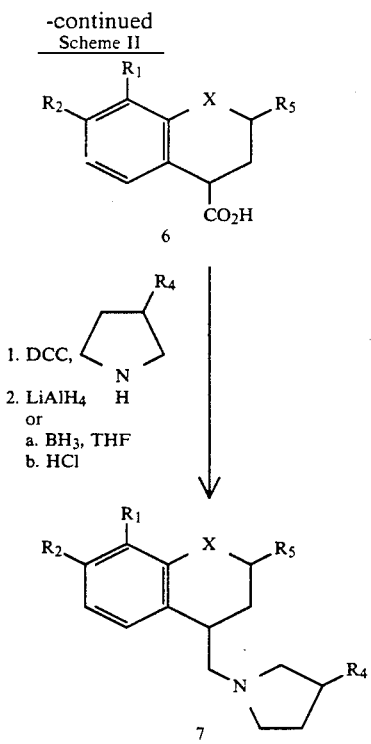

The foregoing may be better understood in connection with the following examples

EXAMPLE 1

7-Methoxy-4-cyano chrom-3-ene

7-Methoxy-4-chromanone (7 g) was added to trimethylsilyl cyanide (TMSCN) (7 ml), $CH_3CN$ (10 ml) and a catalytic amount of $ZnI_2$ and refluxed for 2 hrs. The reaction was cooled, evaporated to dryness, then isopropyl alcohol saturated with HCl(g) (100 ml) was added and this solution refluxed 2 hrs. The reaction was cooled, evaporated to dryness, and saturated aqueous NaCl added. This was then extracted with $CH_2Cl_2$, the organic layer separated, dried ($Na_2SO_4$), filtered and evaporated affording 7.1 g of product. $IR(CHCl_3)$: 2218 $cm^{-1}$.

EXAMPLE 2

4-(Aminomethyl)-7-methoxy chroman

The product from Example 1 was hydrogenated with RaNi in MeOH and $NH_3$ at 4 atm. pressure and gave the desired product, $(M+H)^+194$.

$^1H$ NMR($CDCl_3$): 2.0 (m, 1H); 2.5 (m,2H); 2.95 (m,2H); 3.8 (s,2H); 4.2 (m,2H); 6.4-7.4 (m,3H).

EXAMPLE 3

4-((N-Methylamino)methyl)-7-methoxy chroman

The product from Example 2 (5 g) was added to ethylformate (10 ml) and toluene (100 ml) then refluxed for 2½ hrs. The solution was evaporated to dryness and then tetrahydrofuran (THF) (100 ml) and $BH_3.THF$ 25.9 ml of a IM THF solution) was added followed by heating for 1½ hrs. The reaction was cooled and 6N HCl (20 ml) was carefully added followed by heating for 1 hr. The THF was evaporated and the reaction made basic with aqueous KOH. The reaction was extracted with $CH_2Cl_2$, the organic layer then separated, dried ($MgSO_4$), filtered and evaporated. The residue was chromatographed on silica gel and eluted with ($EtOAc:H_2O:HCO_2H$) (16:2:2), giving the product (1.4 g). Mass spec: $(M+H)^+208$ $^1H$ NMR($CDCl_3$): 2.0 (m,2H); 2.49 (s,3H); 2.8 (m,2H); 3.75 (s,3H); 4.2 (m,1H); 6.38-7.25 (m,3H).

EXAMPLE 4

4-((N-Methylamino)methyl-N-(2-(m-chlorophenyl)ethyl))-7-methoxy chroman hydrochloride The product from Example 3 (1.4 q) was added to dicyclohexylcarbodiimide (DCC) (1.3 g), 1-hydroxybenzotriazole hydrate (1.62 g), m-chlorophenylacetic acid (1.02 g) and dry THF (40 ml). The reaction was stirred at room temperature overnight, then filtered and evaporated to dryness, giving the desired amide. The amide was reduced with $BH_3.THF$ (1M THF solution), followed by treatment with methanolic HCl, to give the desired product, m.p. 185°-86° C., 1.5 g. Mass spec: $(M+H)^+346$. Anal.Calcd. for $C_{20}H_{24}:ClNO_2$: C 62.83; H 6.33; N 3.66. Found: C 62.65; H 6.60; N 3.64. $^1H$ NMR(DMSO-$d_6$): 2.0-2.4 (m,2H); 2.9 (m,2H); 3.1-3.5 (m,4H); 3.7 (s,3H); 4.15 (m,1H); 6.3-7.5 (m,7H).

EXAMPLE 5

4-((N-Ethylamino)methyl)-7-methoxy chroman

The product from Example 2 was reacted as described in Example 3 replacing ethylformate with acetic anhydride, giving the desired product, $(M+H)^+222$. $^1H$ NMR($CDCl_3$): 1.15 (t,3H); 2.05 (m,2H); 2.6-2.0 (m,4H); 3.75 (s,3H); 4.2 (m,1H), 6.3-7.1 (m,3H).

EXAMPLE 6

4-((N-Ethylamino)methyl-N-(2-(m-chlorophenyl)ethyl))-7-methoxy chroman hydrochloride The product from Example 5 was reacted as described in Example 4 to give the desired product, m.p. 148°-149° C. Mass spec: $(M+H)^+360$. Anal.Calcd. for $C_{21}H_{27}Cl_2NO_2.\frac{1}{2} H_2O$: C 62.22; H, 6.96; N 3.46; Found: C 61.87; H 6.68; N 3.38. $^1H$ NMR(DMSO-$d_6$); 1.3 (m,3H); 2.2 (m,2H); 3.0-3.6 (m,6H); 3.7 (s,3H); 4.2 (m,1H); 6.3 7.5 (m,7H).

EXAMPLE 7

4-((N-Methylamino)methyl-N-(2-(2-thienyl)ethyl))-7-methoxy chroman hydrochloride Using the procedure described in Example 4, but replacing m-chlorophenylacetic acid with 2-thiophene acetic acid and the product of Example 3 gave the desired product, m.p. 223°-224° C. Anal. calcd. for $C_{18}H_{24}ClNO_2S$: C 61.09; H 6.84; N 3.96; Found: C 61.17; H 6.82; N 3.93.

EXAMPLE 8

4-((N-Methylamino)methyl-N-(2-(2-furyl)ethyl))-7-methoxy chroman hydrochloride Using the product of Example 3 and the procedure described in Example 4, but replacing m-chlorophenylacetic acid with 2-furylacetic acid and replacing the $BH_3.THF$ reduction with a lithium aluminum hydride reduction gave the desired compound.

EXAMPLE 9

7,8-Dimethoxy-4-cyano thiochrom-3-ene

Using the procedure of Example 1, but replacing 7-methoxy-4-chromanone with 7,8-dimethoxy-4-thiochromanone gave the desired product, m.p. 134°–35° C. Mass spec: $(M+H)+233$. $IR(CHCl_3)$: 2215 cm$^{-1}$(CN).

EXAMPLE 10

7,8-Dimethoxy-4-cyano thiochroman

The product from Example 9(8 g) was dissolved in EtOH (150 ml), then NaBH$_4$ (6.48 g) was added. The reaction was refluxed for 1 hr, cooled and evaporated to dryness. A 10% aqueous HCl solution was added, followed by a methylene chloride extraction. The organic layer was separated, dried (Na$_2$SO$_4$), filtered and evaporated giving the desired product, m.p. 116°–118° C., 5.25 g. Mass spec: $(M+H)+235$ $IR(CHCl_3)$: 2220$^{-1}$ cm (CN).

EXAMPLE 11

4-(Aminomethyl)-7,8-dimethoxy thiochroman hydrochloride

The product from Example 10 (2.35 g) was dissolved in dry THF (50 ml) then 1M BH$_3$.THF in THF (56 ml) was added, followed by refluxing for 3 hrs. The reaction was cooled and methanolic HCl carefully added. The solvents were removed affording after recrystallization from EtOH/Et$_2$O a white solid, 1.9 g, m.p. 254°–55° C. Mass spec.: $(M+H)+239$. $^1$H NMR(DMSO-d$_6$): 1.8 (m,2H); 2.4 (m,2H); 2.8–3.1 (m,5H); 3.2 (m,2H); 3.65–3.8 (d, 6H); 6.8 7.0 (q,2H).

EXAMPLE 12

4-((N-Methylamino)methyl)-7,8-dimethoxy thiochroman hydrochloride

Using the procedure of Example 3 and the product from Example 11, the desired product was obtained, m.p. 176°–77° C. Mass spec.: $(M+H)+253$ $^1$H NMR(DMSO-d$_6$): 1.8 (m,2H); 2.4 (m,2H); 2.8–3.2 (m,5H); 3.3 (m,2H); 3.6–3.8 (d,6H); 6.8–7.0 (q,2H).

EXAMPLE 13

4-((N-Methylamino)methyl-N-(2-(2-thienyl)ethyl))-7,8-dimethoxy thiochroman hydrochloride 2-Thiopheneacetic acid (12.4 g), and NaBH$_4$ (1.4 g) were added to toluene (50 ml) and stirred at room temperature for 2 hrs. Then the product (free base) (1.6 q) from Example 12 was added and the reaction refluxed for 2 hrs., then cooled. Toluene, containing aqueous 10% NaOH was added and the layers separated. The organic layer was dried and evaporated to dryness. The residue was dissolved in EtOH and ethereal HCl added. The solid was filtered and recrystallized from EtOH-/Et$_2$O, affording the desired product, m.p. (226°–27° C., 1.46 g. Mass spec.: $(M+H)+363$. Anal. Calcd. for C$_{19}$H$_{26}$ClNO$_2$S$_2$: H 57.05; H 6.55; N 3.5; Found: C 56.43; H 6.24, N 3.06. $^1$H NMR(DMSO-d$_6$): 1.8 (m,2H); 2.55 (m,2H); 2.9 (m,4H); 3.1 (m,2H); 3.4 (m,5H); 3.65–3.8 (d,6H); 6.88–7.4 (m,4H).

EXAMPLE 14

7-Methoxy-4-cyano thiochromene

Using the procedure of Example 1 but replacing 7-methoxy-4-chromanone with 7-methoxy-4-thiochroma- none gave the desired product, $M+203$ $IR(CHCl_3)$: 2020$^{-1}$ cm (CN).

EXAMPLE 15

4-((N-Methylamino)methyl-N-(2-(2-thienyl)ethyl))-7-methoxy thiochroman hydrochloride Using the product from Example 14 and following the procedures described in Examples 10–13 gave the desired compound, m p. 217°–18° C. Anal. Calcd. for C$_{18}$H$_{24}$ClNOS$_2$: C 58.44; H 6.54; N 3.79; Found: C 58.62; H 6.75; N 3.64. $^1$H NMR(DMSO-d$_6$): 1.85 (m,1H); 2.65 (m,2H); 2.9 (m,2H); 3.35 (m,6H) 3.35 (s,3H); 3.7 (s,3H) 6.6–7.4 (m,6H).

EXAMPLE 16

Using the product from Example 14 and following the procedures described in Examples 10–13 but replacing 2-thiopheneacetic acid with the desired readily available carboxylic acid, the following compounds were prepared:

6a) 4-[(N-Methylamino)methyl-N-(2-(phenyl)ethyl)]-7-methoxy thiochroman hydrochloride.
16b) 4-[(N-methylamino)methyl-N-(2-(m-fluorophenyl)ethyl)]-7-methoxy thiochroman hydrochloride.
16c) 4-[(N-methylamino)methyl-N-(2-(m-chlorophenyl)ethyl)]-7-methoxy thiochroman hydrochloride.

EXAMPLE 17

7-Methoxy-8-methyl-4-cyano chrom-3-ene

Using the procedure described in Example 1 but replacing 7-methoxy-4-chromanone with 7-methoxy-8-methyl-4-chromanone gave the desired product. $IR(CHCl_3)$: 2240 cm$^{-1}$ (CN).

EXAMPLE 18

4-((N-Methylamino)methyl N-(2-(m-chlorophenyl)ethyl))-7-methoxy-8-methyl chroman hydrochloride Using the product from Example 17 and following the procedures described in Examples 2–4 gave the desired compound.

EXAMPLE 19

7-Chloro-4-cyano chrom-3-ene

Using the procedure described in Example 1 but replacing 7-methoxy-4-chromanone with 7-chloro-4-chromanone gave the desired compound.

EXAMPLE 20

4-(Aminomethyl)-7-chloro chroman hydrochloride

Using the product from Example 19 and following the procedures described in Examples 10 and 11 gave the desired compound.

EXAMPLE 21

4-((N-Methylamino)methyl)-7-chloro chroman hydrochloride

Using the procedure of Example 3 and the product from Example 20 gave the desired compound.

EXAMPLE 22

4-((N-Methylamino)methyl-N-(2-(m-methoxyphenyl)ethyl))-7-chloro chroman hydrochloride Using the product from Example 21 and the procedure described in Example 4 but replacing m-chlorophenylacetic acid with m-methoxyphenylacetic acid gave the desired compound.

EXAMPLE 23

4-(Aminomethyl)-7,8-dimethoxy chroman hydrochloride

Using the procedures described in Examples 1–3, but replacing 7-methoxy 4-chromanone with 7,8-dimethoxy-4-chromanone, gave the desired product.

EXAMPLE 24

4-((N-Methylamino)methyl)-7,8-dimethoxy chroman hydrochloride

Using the procedure of Example 3 with the product of Example 23 gave the desired compound.

EXAMPLE 25

4-((N-Methylamino)methyl-N-(2-(m-fluorophenyl)ethyl))-7,8-dimethoxy chroman hydrochloride Using the product of Example 24 and the procedure described in Example 4, but replacing m-chlorophenylacetic acid with m-fluorophenylacetic acid, gave the desired compound, m.p. 195°–197° C. Anal. cald. for $C_{21}H_{27}ClFNO_3$: C 63.71; H 6.87; N 3.54. Found: C 63.95; H 6.95; N 3.59.

EXAMPLE 26

4-((N-Methylamino)methyl-N-(2-(2-thienyl)ethyl)) 7,8-dimethoxy chroman hydrochloride Using the product of Example 24 and the procedure described in Example 4, but replacing m-chlorophenylacetic acid with 2 thiopheneacetic acid, gave the desired compound, m.p. 232°–234° C. Anal. cald. for $C_{19}H_{26}ClNO_3S$: C 59.44; H 6.83; N 3.65. Found: C 59.41; H 6.76; N 3.64.

EXAMPLE 27

4-((N-Ethylamino)methyl)-7-methoxy-8-methyl chroman

Using the procedures described in Examples 1–3 and 5, but replacing 7-methoxy-4-chromanone with 7-methoxy-8-methyl-4-chromanone, gave the desired product, $(M+H)^+346$. $^1H$ NMR($CDCl_3$): 1.15 (t,3H); 2.0 (m,2H); 2.1 (s,3H); 2.8 (m,6H); 3.8 (s,3H); 4.2 (m,1H); 6.45–7.0 (q,2H).

EXAMPLE 28

4-((N-Ethylamino)methyl-N-(2-(2-thienyl)ethyl))-7-methoxy-8-methyl chroman hydrochloride The product of Example 27 was reacted as described in Example 4, but replacing m-chlorophenylacetic acid with 2-thiopheneacetic acid, to give the desired product, m.p. 175°–76° C. Anal. Calcd. for $C_{20}H_{28}ClNO_2S$: C 62.89; H 7.39; N 3.67; Found C 62.60; H 7.41; N 3.63. $^1H$ NMR(DMSO-$d_6$): 1.15 (m,3H); 1.95 (s,3H); 2.1 (m,2H); 2.3 (m,2H); 3.4 (m,8H); 3.75 (s,3H); 4.2 (m,1H); 6.5–7.5 (m,5H).

EXAMPLE 29

4-((N-Methylamino)methyl)-2-phenyl-7-methoxy chroman hydrochloride

Using the procedures described in Examples 1, 10 and 11, but replacing 7-methoxy-4-chromanone with 7-methoxy-2-phenyl-4-chromanone, gave the desired product, $(M+H)^+284$, m.p. 207°–208° C. Anal. Calcd. for $C_{18}H_{22}ClNO_2$: C 67.60; H 6.93; N 4.38; Found: C 67.46; H 6.83; N 4.33. $^1H$ NMR(DMSO-$d_6$) 1.9 (m,3H); 2.6 (m,2H); 3.35 (s,3H); 3.7 (s,3H); 5.1 (q,1H); 6.4–7.6 (m,8H).

EXAMPLE 30

4-((N-Methylamino)methyl-N-(2-(2-thienyl)ethyl))-7-methoxy-2-phenyl chroman hydrochloride The product of Example 29 was reacted as described in Example 4, but replacing m-chlorophenylacetic acid with 2-thiopheneacetic acid, giving the desired compound as an amorphous solid. Mass spec.: $(M+H)^+394$ Anal cald. for $C_{24}H_{28}ClNO_2S \cdot \frac{1}{2}H_2O$: % C 65.66; H 6.66; N 3.19. Found: % C 65.27; H 6.51; N 3.00.

EXAMPLE 31

4-((N-Methylamino)methyl)-7-methoxy-2-methyl chroman

Using the procedures described in Examples 1–3, but replacing 7-methoxy-4-chromanone with 7-methoxy-2-methyl-4-chromanone, gave the desired compound. $(M+H)^+220$.

EXAMPLE 32

4-((N-Methylamino)methyl-N-(2-(2-thienyl)ethyl)) 7-methoxy-2-methyl chroman hydrochloride The product of Example 31 was reacted as described in Example 4, replacing m-chlorophenylacetic acid with 2-thiopheneacetic acid, giving the desired compound.

EXAMPLE 33

4-((N-methylamino)methyl-N-(2-(m-methoxyphenyl)ethyl)-7-methoxy-2-methyl chroman hydrochloride The product of Example 31 was reacted as described in Example 4 replacing m-clorophenylacetic acid with m-methoxyphenylacetic acid to give the desired product.

EXAMPLE 34

4-((N-Methylamino)methyl-N (2 (m-fluorophenyl)ethyl))-7,8-dihydroxy chroman hydrobromide The product of Example 25 was treated at $-78°$ C. with $BBr_3$ in $CH_2Cl_2$. The reaction mixture was allowed to warm to 0° C. and stirred for 3 hours under nitrogen. The reaction mixture was cooled to $-78°$ C., then carefully quenched with MeOH. The reaction mixture was evaporated to dryness, triturated with ether, and filtered to give the desired product.

EXAMPLE 35

4-((N-Methylamino)methyl-N-(2 (m-chlorophenyl)ethyl))-7-methoxy-2-phenyl chroman hydrochloride The product of Example 29 was reacted as described in Example 4 to afford the desired compound.

EXAMPLE 36

4-((N-Methylamino)methyl-N-(2-(m-chlorophenyl)ethyl))-7-hydroxy-2-phenyl chroman hydrobromide The product of Example 35 was reacted as described in Example 34 to give the desired compound.

EXAMPLE 37

7,8-Methylenedioxy-4-chromanone

To a solution of 2,3-methylenedioxyphenol (27 g) and N-methyl morpholine (19.6 g) in THF (100 ml) was added benzyl propiolate (28 g) over a period of 30 minutes with cooling. After the addition was complete the reaction was stirred at room temperature for 1.5 hours followed by concentration The residue was taken up into $Et_2O$ (500 ml), washed with 10% HCl (2×100 ml), dried over $MgSO_4$. filtered and concentrated. This material was subjected to hydrogenation with 10%Pd/C in methanol at 4 atm. The reaction was filtered and concentrated. The resulting saturated acid was dissolved into methanesulfonic acid (350 ml) and stirred for 24 hours. The reaction was poured onto ice and extracted with $CH_2Cl_2$. The organic layer was washed with saturated $Na_2CO_3$, dried over $MgSO_4$, filtered and concentrated to provide the desired material.

EXAMPLE 38

4-((N-Methylamino)methyl-N-(2-(2-thienyl)ethyl))-7,8-methylenedioxychroman hydrochloride Using the procedures in Examples 1-4 but replacing 7-methoxy-4-chromanone with Example 37 and replacing m-chlorophenylacetic acid with thiopheneacetic acid afforded the desired product.

EXAMPLE 39

4-((N-Methylamino)methyl-N-(2-phenethyl))-7,8-methylenedioxychroman hydrochloride Using the procedures outlined in Example 38 but replacing thiopheneacetic acid with phenylacetic acid provided the desired product.

EXAMPLE 40

4-((N-Ethylamino)methyl-N-(2-(2-thienyl)ethyl))-7,8-methylenedioxychroman hydrochloride Using the procedures in Examples 1, 2, 5 and 4 but replacing 7-methoxy-4-chromanone with Example 37 and replacing m-chlorophenylacetic acid with thiopheneacetic acid afforded the desired product.

EXAMPLE 41

4-((N-Ethylamino)methyl-N (2 phenethyl)) 7,8-methylenedioxychroman hydrochloride Using the procedures in Examples 1, 2, 5 and 4 but replacing 7-methoxy-4-chromanone with Example 37 and replacing m-chlorophenylacetic acid with phenylacetic acid provided the desired product.

EXAMPLE 42

7,8-Ethylenedioxy-4-chromanone

Using the procedure outlined in Example 37 but replacing 2,3-methylenedioxyphenol with 2,3-ethylenedioxyphenol provided the desired material.

EXAMPLE 43

4-((N-Methylamino)methyl-N-(2-(2-thienyl)ethyl))-7,8-ethylenedioxychroman hydrochloride Using the procedures in Examples 1-4 but replacing 7-methoxy-4-chromanone with Example 42 and replacing m-chlorophenylacetic acid with thiopheneacetic acid afforded the desired product.

EXAMPLE 44

4-((N-Methylamino)methyl-N-(2-phenethyl))-7,8-ethylenedioxychroman hydrochloride Using the procedures in Examples 1.4 but replacing 7-methoxy-4-chromanone with Example 42 and replacing m-chlorophenylacetic acid with phenylacetic acid afforded the desired product.

EXAMPLE 45

4-((N-Ethylamino)methyl-N (2-(2-thienyl)ethyl))-7,8-ethylenedioxychoman hydrochloride Using the procedures in Examples 1, 2, 5 and 4 but replacing 7-methoxy-4-chromanone with Example 42 and replacing m-chlorophenylacetic acid with thiopheneacetic acid afforded the desired product.

EXAMPLE 46

4-((N-Ethylamino)methyl-N-(2-phenethyl)) 7,8-ethylenedioxychroman hydrochloride Using the procedures in Examples 1, 2, 5 and 4 but replacing 7-methoxy-4-chromanone with Example 42 and replacing m-chlorophenylacetic acid with phenylacetic acid provided the desired product.

EXAMPLE 47

4-Carboxy-7,8-methylenedioxychroman

Using the procedure in Example 1, but replacing 7-methoxy-4-chromanone wih Example 37 afforded the unsaturated nitrile To a solution of this nitrile (5.0 g) in ethanol (80 ml) was added in small portions sodium borohydride (1.44 g). After the addition was complete the reaction was heated to reflux. After 12 hours, the reaction was cooled and concentrated. The residue was taken up into 1 N HCl and $CH_2Cl_2$ and the layers separated. The organic phase was washed with water, brine, dried over $MgSO_4$, filtered and concentrated. The resulting material was dissolved into ethylene glycol (42 ml) treated with 45% KOH (30 ml) and heated to reflux. After 3 hours the reaction was cooled with an ice bath, diluted with ice/water and acidified with concentrated HCl. The product was extracted with ethyl acetate (3×75 ml), washed with brine, dried over $MgSO_4$, filtered and concentrated to afford the desired product.

EXAMPLE 48

7,8-Methylenedioxy-4-(3-(2-thienyl)pyrrolindino-1-methyl) chroman hydrochloride Using the procedure in Example 4 but replacing m-chlorophenylacetic acid with Example 47 and Example 3 with 3-(2-thienyl)pyrrolidine afforded the desired material.

EXAMPLE 49

7,8-Methylenedioxy 4-(3-phenylpyrrolindino-1-methyl) chroman hydrochloride

Using the procedure in Example 4 but replacing m-chlorophenylacetic acid with Example 47 and Example 3 with 3-phenylpyrrolidine afforded the desired material.

EXAMPLE 50

4-Carboxy-7,8-ethylenedioxychroman

Using the procedure in Example 47 but replacing Example 37 with Example 42 provided the desired material.

EXAMPLE 51

7,8-Ethylenedioxy-4-(3-(2-thienyl)pyrrolindino-1-methyl) chroman hydrochloride

Using the procedure in Example 4 but replacing m-chlorophenylacetic acid with Example 49 and Example 3 with 3-(2-thienyl)pyrrolidine afforded the desired material.

EXAMPLE 52

7,8-Ethylenedioxy-4-(3-phenylpyrrolindino-1-methyl) chroman hydrochloride

Using the procedure in Example 4 but replacing m-chlorophenylacetic acid with Example 49 and Example 3 with 3-phenylpyrrolidine afforded the desired material.

The compounds were assessed for alpha-adrenergic receptor subtype selectivity by use of radioligand binding techniques as described previously (DeBernardis et. al. J. Med. Chem. 28, 1398 (1985)). Affinity for the alpha-1-receptor was assessed using rat liver homogenates and the radioligand [$^3$H]-prazosin; whereas for the alpha-2-receptor, rat cerebral cortices and the radioligand [$^3$H]-rauwolscine were utilized. Results obtained from the binding studies are shown in Table 1 for a representative sample of compounds disclosed herein.

TABLE 1

Radioligand Binding Data at alpha 1- and alpha 2- Adrenoceptors for Representative Compounds

| Example # | $K_i$ (nM) alpha-1 | $K_i$ (nM) alpha-2 | alpha-2 - Selectivity $K_i$ alpha-1/$K_i$ alpha-2 |
|---|---|---|---|
| 4 | 260 | 24 | 11 |
| 6 | 1135 | 34 | 33 |
| 7 | 590 | 10 | 59 |
| 13 | 96 | 3 | 32 |
| 25 | 550 | 3 | 183 |
| 26 | 10000 | 5.8 | 1724 |
| 28 | 1000 | 34 | 29 |

The compounds of the invention can be administered in any effective pharmaceutically acceptable form to warm blooded animals, e.g., in oral, parenteral or infusable dosage forms, or as a buccal or nasal spray. Suitable parenteral routes of administration include, for example, intramuscular, intravenous, intraperitoneal or subcutaneous administration of the compounds.

In addition to the active compounds, compositions according to this invention for parenteral injection may comprise pharmaceutically acceptable sterile aqueous or nonaqueous solutions, suspensions or emulsions. Examples of suitable nonaqueous carriers, diluents, solvents or vehicles include propylene glycol, polyethylene glycol, vegetable oils, such as olive oil, and injectable organic esters such as ethyl oleate. Such compositions may also contain adjuvants such as preserving, wetting, emulsifying, and dispersing agents. They may be sterilized, for example, by filtration through a bacteria-retaining filter, or by incorporating sterilizing agents into the compositions. They can also be manufactured in the form of sterile solid compositions which can be dissolved in sterile water, or other sterile injectable medium, immediately before use.

Solid dosage forms for oral administration include capsules, tablets, pills, powders and granules. In such solid dosage forms, the active compound may be admixed with at least one inert diluent such as sucrose, lactose or starch. Such dosage forms may also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups and elixirs containing inert diluents commonly used in the art, such as water. Besides such inert diluents, compositions may also comprise adjuvants, such as wetting agents, emulsifying and suspending agents, and sweetening. flavoring and perfuming agents.

Actual dosage levels of active ingredient in the compositions of the invention may be varied so as to obtain an amount of active ingredient effective to obtain a desired therapeutic response for a particular composition and method of administration. The selected dosage level therefore depends upon the desired therapeutic effect, on the route of administration, on the desired duration of treatment and other factors. Generally, dosage levels of about 0.1 to about 200, more preferably about 0.5 to about 150 and most preferrably about 1 to about 125 mg of active ingredient per kg of body weight per day are administered orally to a mammalian patient suffering from depression. If desired, the daily dose may be divided into multiple doses for administration, e.g., two to four separate doses per day.

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A compound of the formula

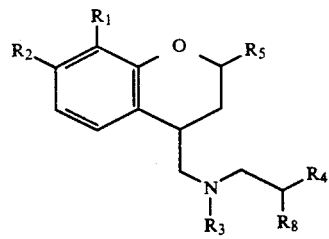

wherein
  $R_1$ and $R_2$ are independently selected from the group consisting of hydrogen, hydroxy, halo, loweralkoxy, thioalkoxy, and loweralkyl;
  $R_3$ is loweralkyl;
  $R_4$ is selected from

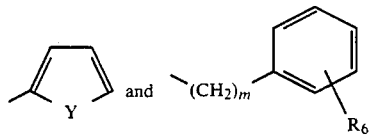

and wherein Y is O or S, R₆ is hydrogen, methoxy or halo, and m is 0 or 1;

R₅ is hydrogen, loweralkyl, phenyl, or substituted phenyl wherein the phenyl ring is substituted with one, two or three substituents independently selected from loweralkyl, halo, hydroxyl, loweralkoxy, amino, and thioalkoxy; and R₈ is hydrogen, or R₃ and R₈ taken together form a pyrrolidine ring; with the proviso that when R₄ is

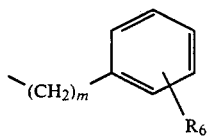

then R₃ and R₈ taken together form a pyrrolidine ring; or a pharmaceutically acceptable salt thereof.

2. A compound of claim 1 wherein $R_1$ is hydrogen or methoxy and $R_2$ is methoxy; $R_3$ is methyl or ethyl; and $R_4$ is furyl, thienyl or $R_3$ and $R_8$ taken together form a pyrrolidinyl ring and $R_4$ is furyl, thienyl, phenyl or substituted phenyl.

3. A compound selected from the group consisting of:
4-((N-methylamino)methyl-N-(2-(2-thienyl)ethyl)-7,8-dimethoxy chroman;
4-((N-methylamino)methyl-N-(2-(2-thienyl)ethyl)-7-methoxy chroman;
4-((N-methylamino)methyl-N-(2-(2-furyl)ethyl)-7-methoxy chroman;
4-((N-ethylamino)methyl-N-(2-(2-thienyl)ethyl)-7-methoxy-8-methyl chroman;
4-((N-methylamino)methyl-N-(2-(2-thienyl)ethyl)-7-methoxy-2-phenyl chroman; and
4-((N-methylamino)methyl-(2-(2-thienyl)ethyl)-7-methoxy-2-methyl chroman; or a pharmaceutically acceptable salt thereof.

4. A pharmaceutical composition for selectively inhibiting alpha-2-adrenergic receptors comprising a pharmaceutically acceptable carrier and a therapeutically effective amount of a compound of claim 1.

5. A method for selectively inhibiting alpha-2-adrenergic receptors comprising administering to a patient in need, a therapeutically effective amount of a compound of claim 1.

6. A method for treating depression comprising administering to a patient in need, a therapeutically effective amount of a compound of claim 1.

* * * * *